United States Patent [19]

Bagan et al.

[11] Patent Number: 4,728,664

[45] Date of Patent: Mar. 1, 1988

[54] UNIQUELY NON-MUTAGENIC SUBSTITUTED NITROIMIDAZOLE

[75] Inventors: Edward S. Bagan, Nutley; Gerald T. Miwa, Maplewood, both of N.J.

[73] Assignee: Merck & Co., Inc., Rahway, N.J.

[21] Appl. No.: 770,129

[22] Filed: Aug. 28, 1985

[51] Int. Cl.$^4$ .............................................. A61K 31/415
[52] U.S. Cl. ...................................................... 514/401
[58] Field of Search ........................................... 514/401

[56] References Cited

U.S. PATENT DOCUMENTS 3,644,392  2/1972  Henry ................................... 548/339

OTHER PUBLICATIONS

*Indian Journal of Chemistry,* Section B, 21B (11), pp. 1006–1021 (1982).
Miwa et al., (I) pp. 527–535, *Biological Reactive Intermediates III,* Kocsis et al. (Ed.) Plenum Publishing Corp., 1986.
Robbie et al., *Am. Obstet. Gynecol.,* 145: 865–879 (1983).
Goldman, *The John Hopkins Medical Journal* 147: 1–9 (1980).
Miwa et al., (II) *Chem. Biol. Ineractions* 50: 189–202 (1984).
*Animal Diseases* USDA Yearbook of Agriculture 1956, p. 462.
*Merck Veterinary Manual,* Fifth Ed., p. 1062 (1979).

*Primary Examiner*—Albert T. Meyers
*Assistant Examiner*—John M. Kilcoyne
*Attorney, Agent, or Firm*—David L. Rose; Michael C. Sudol, Jr.

[57] ABSTRACT

There is disclosed a substituted nitroimidazole compound, 1-methyl-2-methylsulfonyl-4-nitroimidazole which is an antiprotozoal and bactericidal compound with the unique and surprising property of being totally non-mutagenic and thus of a much higher degree of safety than is found with other nitroimidazoles. Compositions and methods for the antiprotozoal and bactericidal uses of such compounds are also disclosed.

2 Claims, No Drawings

UNIQUELY NON-MUTAGENIC SUBSTITUTED NITROIMIDAZOLE

BACKGROUND OF THE INVENTION

The compound 1-methyl-2-methylsulfonyl-4-nitroimidazole is a known compound having been disclosed in the Indian Journal of Chemistry, Section B, 21B (11), pp. 1006-21. The compound was published only with respect to spectral studies thereof and no mention was made of its biological activities or relative mutagenicity.

SUMMARY OF THE INVENTION

This invention is concerned with 1-methyl-2-methylsulfonyl-4-nitroimidazole as an antiprotozoal and bactericidal agent with unique safety due to an undetectable level of mutagenic activity in standard mutagenicity tests. Thus it is an object of this invention to describe such a compound and its preparation. A further object is to describe the biological activity and the mutagenicity tests for such compounds. A still further object is to describe compositions containing such compound as the active component thereof. Further objects will become apparent from a reading of the following description.

DESCRIPTION OF THE INVENTION

The compound 1-methyl-2-methylsulfonyl-4-nitroimidazole has the following structure:

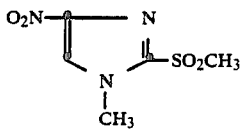

The compound may conveniently be prepared from the corresponding 5-nitroimidazole in a rearrangement reaction using, for example, potassium iodide in a solvent such as N,N-dimethylformamide. The reaction is heated at a temperature up to the reflux temperature of the reaction mixture, or temperatures in excess of its reflux temperature in a pressure vessel. The heating is conveniently carried out for from 1 to 4 hours and upon cooling, the product is isolated using standard techniques.

Nitroimidazoles are known generally to be mutagenic compounds and are usable only in those instances where the disease being treated is of such a level of seriousness that the negative effects of the mutagenicity of the compound are balanced against the conditions resulting from the disease. Thus, the discovery of a non-mutagenic drug which could be used to treat protozoal diseases has been long sought.

One very well accepted measure of the mutagenicity of chemicals, which has generally also been closely correlated with the carcinogenicity of such compounds, is the Ames Mutagenicity Test. This test involves the addition to a fermentation medium in which is growing a particular organism identified as Ames Salmonella TA100, and measuring the number of mutant organisms formed. Greater numbers of mutants over the background number of spontaneous mutants is an indication of greater mutagenicity of the compound. Generally a series of varying concentrations of the test compound is employed to determine threshold levels if possible.

In one such Ames mutagenicity test 1-methyl-2-methylsulfonyl-4-nitroimidazole was compared to two commercially available nitroimidazoles, ronidazole (1-methyl-2-[(carbamoyloxy)methyl]-5-nitroimidazole) and metronidazole (1-(2-hydroxyethyl-2-methyl-5-nitroimidazole). At 3 $\mu$g per plate ronidazole had 358 mutants per plate while metronidazole and the instant compound were indistinguishable from background. At 30 $\mu$g per plate, ronidazole had 2682 mutants per plate and metronidazole had 142 mutants per plate while the instant compound was still indistinguishable from background. At 100 and 300 $\mu$g per plate metronidazole had 443 and 1374 mutants per plate respectively, while the instant compound was still at barely a threshold level of 30 and 65 mutants per plate respectively. The instant compound continued to show no more than a threshold level at 400, 500 and 600 $\mu$g per plate by recording 0, 54 and 0 mutants per plate respectively. Such levels of mutagenicity are not statistically significantly different from background and as such, the instant compound would be considered non-mutagenic.

Thus, considering the rapidly increasing mutagenic activity of ronidazole and metronidazole and the continuing statistically insignificant levels of mutagenic activity with the instant compound, it is apparent that the instant compound represents a considerable breakthrough in treating protozoal and bacterial diseases with a new level of safety, unachieved and unachievable with prior therapies.

The instant compound has antiprotozoal and antibacterial activity, and is particularly active against the causative organisms of the protozoal parasitic diseases trichomoniasis and enterohepatitis. It is also effective against amoebiasis and trypanosomiasis, as well as against the PPLO (Pleuropneumonia-like organisms) and schistosomes.

Trichomoniasis is a protozoan disease caused by parasites of the genus Trichomonas. The compound of the invention is effective against the particularly troublesome form of trichomoniasis known as *T. vaginalis* vaginitis, caused by infestation of the vagina with *T. vaginalis*. In treating this disease, the compound may be administered either orally or topically. For oral administration unit dosage, forms such as tablets or capsules are normally employed which may contain from about 50 to about 500 mg of active ingredient. These are prepared by techniques known in the art, and contain the usual diluents, granulating agents, extenders and/or lubricating agents known to be satisfactory for the compounding of tablets and capsules.

It is preferred to administer the compound of the invention orally at a dose level of from about 25-1000 mg/day, in either single or divided doses with divided doses being used more frequently than a single dose. An example of a suitable compressed tablet is the following:

| Component: | Mg per tablet |
| --- | --- |
| 1-methyl-2-methylsulfonyl-4-nitroimidazole | 250 |
| Dicalcium phosphate | 100 |
| Lactose | 75 |
| Starch | 50 |
| Guar gum | 12 |
| Magnesium stearate | 2-3 |

If desired, tablets may be sugar coated or enteric coated by standard techniques. Alternatively, the antitrichomonal agent may be formulated in capsule form using fillers such as lactose, starch or kaolin. A typical capsule would contain 250 mg of, for instance, 1-methyl-2-methylsulfonyl-4-nitroimidazole, 2-3 mg of magnesium stearate and about 75 mg of lactose in a No. 0 size capsule. Tablets and capsules containing smaller quantities of active ingredient may be made by reducing proportionately the amounts of excipients and diluents illustrated above. Alternatively, the compound may be administered orally in liquid pharmaceutical vehicles such as solutions, emulsions, syrups or suspensions containing the diluents, flavoring agents and preservatives customarily employed in the pharmaceutical art.

For topical application, creams or suppositories containing the active ingredient may be used. To illustrate, a cream is prepared by mixing sufficient quantities of hydrophilic ointment and water, containing from about 5-10% by weight of the compound, in sufficient quantities to produce a cream having the desired consistency.

Enterohepatitis is a disease occurring primarily in turkeys and is caused by the protozoan parasite *Histomonas meleagridis*. It is also known as turkey blackhead disease. The compound of this invention is useful in the prevention and treatment of this disease and for this purpose is administered to turkeys mixed with an element of turkey sustenance, i.e. in the feed or drinking water. Although the optimum dose level will depend on the severity of the infection, good control of enterohepatitis is obtained by orally administering to the turkeys a feed containing from about 0.003% to about 0.1% by weight of the instant compound. When the material is administered via the drinking water, somewhat higher levels may be employed, especially for therapeutic use. For instance, the drinking water may contain up to about 0.2% by weight of the active ingredient with good results.

As previously stated, the compound described herein may also be employed against trypanosomiasis, amoebiasis and the pleuro-pneumonia like organisms which have come to be known as PPLO.

The compound is effective against PPLO when the compound is administered to fowl or swine in feed containing from about 0.003% to about 0.1% by weight of the compound. The preferred dosage level, however, is between from about 0.003% to 0.08% by weight.

When used as antibacterial agents, the instant compound may be formulated in oral and topical dosage forms, at the dosage levels discussed above with respect to trichomoniasis.

The following example is provided in order that the invention might be more fully understood. It should not be construed as being limitative.

Potassium iodide (4.8 g) and 1-methyl-2-methylsulfonyl-5-nitroimidazole (5.0 g) were combined in N,N-dimethylformamide (30 ml) and the reaction mixture heated to 160° C. for 2 hours. Upon cooling, the reaction mixture was added to 150 ml of a water and ice mixture. The product precipitated and was filtered and dried affording 4.4 g of 1-methyl-2-methylsulfonyl-4-nitroimidazole.

What is claimed is:

1. A method for the non-mutagenic treatment of the protozoal and bacterial diseases trichomoniasis, amoebiasis, trypanosomiasis, enterohepatitis, and schistosome and pleuro-pneumonia like organism infections in animals requiring treatment for such diseases which comprises orally or topically administering from 25 to 1000 mg per day of 1-methyl-2-methylsulfonyl-4-nitroimidazole.

2. The method of claim 1 wherein the disease is trichomoniasis, amoebiasis, trypanosomiasis, enterohepatitis or pleuro-pneumonia-like organism infection.

* * * * *